(12) United States Patent
Peyman (10) Patent No.: US 6,432,078 B1
(45) Date of Patent: Aug. 13, 2002

(54) SYSTEM AND METHOD FOR REMOVING CATARACT OR OTHER CELLS IN AN EYE USING WATER JET AND SUCTION (76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 89 days.

(21) Appl. No.: 09/597,737

(22) Filed: Jun. 19, 2000

(51) Int. Cl.$^7$ ................................................ A61M 1/00
(52) U.S. Cl. ........................... 604/27; 604/28; 604/30; 604/31; 604/35; 604/43; 604/294; 128/276; 128/305; 128/24 A; 606/107
(58) Field of Search ............................. 604/30, 31, 35, 604/43, 294, 27, 28; 128/276, 305, 24 A; 606/107

(56) References Cited

U.S. PATENT DOCUMENTS

| | | | | |
|---|---|---|---|---|
| 3,589,363 A | * | 6/1971 | Banko ........................ 128/24 A |
| 3,930,505 A | * | 1/1976 | Wallach ....................... 128/305 |
| 4,465,470 A | * | 8/1984 | Kelman ........................ 604/27 |
| 4,911,163 A | | 3/1990 | Fina |
| 5,154,696 A | * | 10/1992 | Shearing ...................... 604/22 |
| 5,290,295 A | | 3/1994 | Querals et al. |
| 5,370,609 A | | 12/1994 | Drasler et al. |
| 5,380,319 A | * | 1/1995 | Saito et al. ................... 606/28 |
| 5,439,446 A | | 8/1995 | Barry |
| 5,476,448 A | * | 12/1995 | Urich .......................... 604/22 |
| 5,496,267 A | | 3/1996 | Drasler et al. |
| 5,514,092 A | | 5/1996 | Forman et al. |
| 5,520,636 A | * | 5/1996 | Korth et al. ................... 604/30 |
| 5,690,641 A | * | 11/1997 | Sorensen et al. ........... 606/107 |
| 5,697,898 A | * | 12/1997 | Devine ........................ 604/22 |
| 5,785,675 A | | 7/1998 | Drasler et al. |
| 5,830,176 A | * | 11/1998 | Mackool ...................... 604/22 |
| 5,851,210 A | | 12/1998 | Torossian |
| 5,885,279 A | * | 3/1999 | Bretton ........................ 606/41 |
| 6,059,809 A | | 5/2000 | Amor et al. |
| 6,066,138 A | | 5/2000 | Sheffer et al. |

* cited by examiner

*Primary Examiner*—Thomas Denion
*Assistant Examiner*—Theresa Trieu
(74) *Attorney, Agent, or Firm*—Roylance,Abrams,Berdo & Goodman, L.L.P.

(57) ABSTRACT

A system and method for removing cataract cells inside of an eye having a heated inflatable brushing device adapted to pass through an incision in the lens capsule, the brush being inflated with a heated fluid after passing through the incision in the lens capsule. The brushing device has an abrasive surface and is coupled to a tube that is adapted to pass through the incision in the eye and kill and dislodge cells therefrom. The tube has a first passageway and a first orifice for infusing a fluid inside of the eye and dislodging cells therein and a second passageway and second orifice for aspirating the fluid and cells out of the eye. The brush device also can be coupled to a motor, which rotates or oscillates the brush device to further dislodge the cells from the incision of the eye, such as from the lens capsule. In another embodiment, the tube can be a closed system having an aperture in the periphery, the aperture extending from the surface of the tube to the first passageway. As a high pressure fluid passes through the first passageway and adjacent the aperture, a suctioning force is created, drawing cells into the first passageway and dislodging the cells from the eye. The cells are then removed from the eye through an interconnected second passageway.

9 Claims, 14 Drawing Sheets

SYSTEM AND METHOD FOR REMOVING CATARACT OR OTHER CELLS IN AN EYE USING WATER JET AND SUCTION

CROSS-REFERENCE TO RELATED APPLICATION

Related subject matter is disclosed in copending U.S. patent application of Gholam A. Peyman entitled "System and Method for Thermally and Chemically Treating Cells at Sites of Interest in the Body to Impede Cell Proliferation", Ser. No. 09/494,248, filed on Jan. 31, 2000, the entire contents of which is incorporated herein by reference.

FIELD OF INVENTION

The present invention relates to a system and method for treating and removing cells in an interior chamber of an eye, such as in the lens capsule of an eye. More particularly the present invention relates to a system and method that treats cataract using a heated balloon to kill and dislodge the cells forming the cataract and a pressurized jet to further dislodge the cataract cells from the eye without or substantially without causing protein denaturation to occur in the cells, and then using an aspirator or return tube for removing the fluid in the eye and the cells dislodged therefrom.

BACKGROUND OF THE INVENTION

Cataract is a condition that creates cloudiness in the lens of an eye, and is one of the major causes of blindness in the developing world. Cataract occurs in the lens of an eye and impedes the lens from focusing light on the retina. The lens is composed of tightly packed lens fibers surrounded by a collagenous elastic capsule. Beneath the lens capsule are epithelial cells, which are responsible for the metabolic function of the lens. Cataract may occur in any or all of these parts of the lens, which results in several different classifications of cataract, namely, subcapsular, cortical, and nuclear. To treat cataract, the cloudy portion of the lens, whether it is in the lens fibers, the epithelial, or both, or in any other portion of the lens, should be surgically removed. Generally, this is attempted by making an incision in the corneal periphery (limbus) to enter the anterior chamber and remove the cataract.

A conventional method for removing cataract in the eye is the (manual) extracapsular technique. In this procedure, the eye is opened at the limbus, and either a bent needle or any other curved sharp edged instrument or special forceps are employed to open the anterior lens capsule and remove the nucleus within the capsule of the lens. Thereafter, the remaining cortical material is removed so as to leave a clear posterior lens capsule in the eye. The capsule provides a barrier between the anterior chamber and the vitreous cavity of the eye, as well as a resting surface for an implanted artificial lens. However, this method results in an incision of about 7 millimeters, creating an open system in the lens capsule. In other words, this method makes any fluid that is irrigated into the lens capsule difficult to retain and remove.

Other types of cell removing techniques, such as phacoemulsification, use a probe containing an ultrasonic wave generator, a rinsing fluid and a suction tip. In the phacoemulsification technique, an incision is made in the cornea of an eye and the probe is inserted. Compacted proteins of the lens nucleus are broken up by ultrasonic power and are emulsified by a rinsing fluid. The emulsified lens proteins as well as soft peripheral lens proteins are removed from the eye by the suction tip. Phacoemulsification is generally considered superior to extracapsular surgery because it only requires a surgical wound of about 2–3 millimeters as opposed to about 7 millimeters. However, the problem with phacoemulsification is that opacification of the remaining capsule or posterior capsular opacification can occur. This opacification is caused by proliferation of the remaining lens epithelium, which this procedure has failed to remove from the remaining capsule entity. An example of this type of technique is disclosed in U.S. Pat. No. 6,066,138 to Sheffer et al., the entire contents of which are incorporated herein by reference.

Several similar techniques exist for treating and removing cells in the body using an aspirator and/or an irrigator. For example, numerous types of devices use a high-pressure water jet to remove plaque deposits from the arterial walls of a patient.

Generally, this technique uses a tube with a high-pressure water jet, an evacuation tube, and a balloon. The balloon is inflated within the blood vessel, holding the tube in the desired position adjacent a plaque deposit. The water jet then ablates the plaque, and evacuates it through the evacuation tube.

Although these conventional systems may be useful for removing tissue in a blood vessel, they are ineffective for removal of cells in the eye. The balloon in the conventional systems would not assist in removing cells or help in killing the cells to impede cell multiplication. Additionally, the balloon's purpose in the existing apparatuses is to hold the device in place, making the movement of the device difficult and less effective for removing cells from inside a lens capsule. Examples of these types of techniques are disclosed in U.S. Pat. No. 4,911,163 to Fina; U.S. Pat. No. 5,290,295 to Querals et al; U.S. Pat. Nos. 5,370,609, 5,496,267, and 5,785,675 all to Drasler et al; U.S. Pat. No. 5,439,446 to Barry; and U.S. Pat. No. 5,514,092 to Forman et al., the entire contents of each are incorporated herein by reference.

Thus, there is a continuing need to improve the systems and methods for removing cataract and preventing unwanted cell proliferation in the eye.

SUMMARY OF THE INVENTION

Accordingly, it is an object of the present invention to provide a system and method for removing cells from an eye, such as cells in the lens epithelium, to eliminate posterior capsular opacification.

Another object of the present invention is to provide a system and method for separating and removing the lens epithelium from the lens capsule substantially simultaneously.

Still another object of the present invention is to provide a system and method for removing cells from the eye that employs an apparatus having a relatively small cross section, thus allowing for a relatively small incision in the lens capsule for entry of the apparatus.

Still another object of the present invention is to provide a system and method for removing cells from the eye that creates a semi-closed system within the lens capsule, allowing for easy irrigation and aspiration of fluid into and out of the eye.

Still another object of the present invention is to provide a system and method for removing cells from the eye that uses a fluid to separate the lens epithelium from the lens capsule and an aspirating device o return tube to remove the lens epithelium and the fluid therefrom.

Yet another object of the present invention is to provide a system and method for removing cells from the eye that utilizes an inflatable brush to assist in killing and separating the lens epithelium from the lens capsule, thus preventing protein denaturation to occur which creates a coagulum that cannot be removed.

The foregoing objects are basically obtained by providing a system for removing cells inside of an eye, comprising an instrument, such as a brush, adapted to pass through an incision in an eye and having an abrasive surface, and a first tube adapted to pass through that or another incision and having a first passageway and a first orifice for infusing a fluid inside of the eye to dislodge cells therein and a second passageway and second orifice for aspirating the fluid and dislodged cells out of the eye.

The foregoing objects are further obtained by providing a high pressure system for removing cells from an interior of an eye, comprising a first passageway having an aperture, the passageway adapted to pass a high pressure fluid therethrough, the high pressure fluid flowing adjacent the aperture and causing a suctioning force through the aperture, the aperture adapted to allow cells to pass therethrough and into the first passageway, and the high pressure fluid adapted to dislodge cells from the eye and a second passageway for removing the fluid and dislodged cells out of the eye.

Other objects, advantages and novel features of the invention will become apparent from the following detailed description, which, taken in conjunction with the annexed drawings, disclose preferred embodiments of the invention.

BRIEF DESCRIPTION OF THE DRAWINGS

Referring to the drawings which form a part of this disclosure.

DETAILED DESCRIPTION OF THE PREFERRED EMBODIMENT

Figure 1:
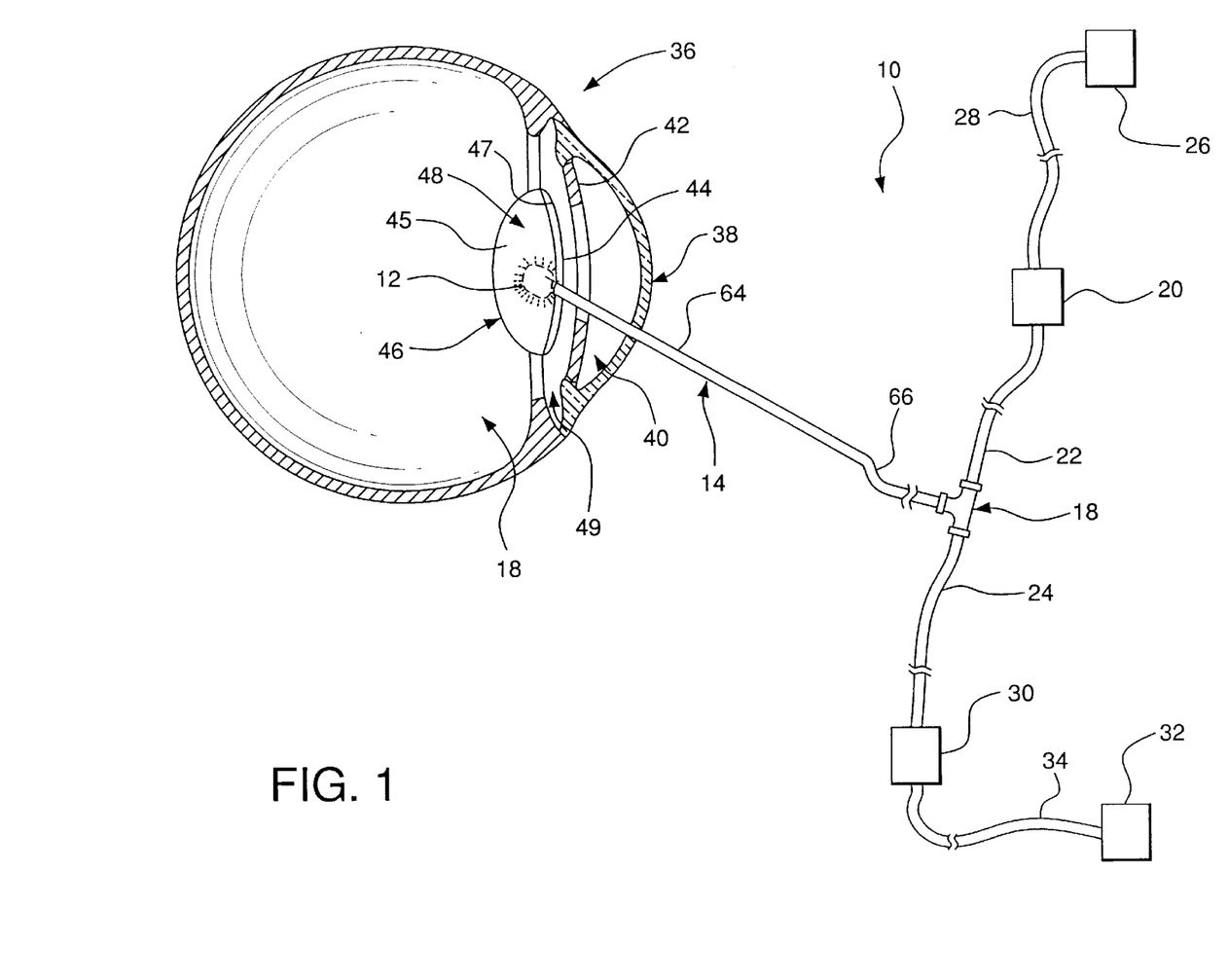
FIG. 1 illustrates a system for removing cells according to an embodiment of the present invention, which is being inserted into the lens capsule of an eye shown in cross-section.
Figure 2:
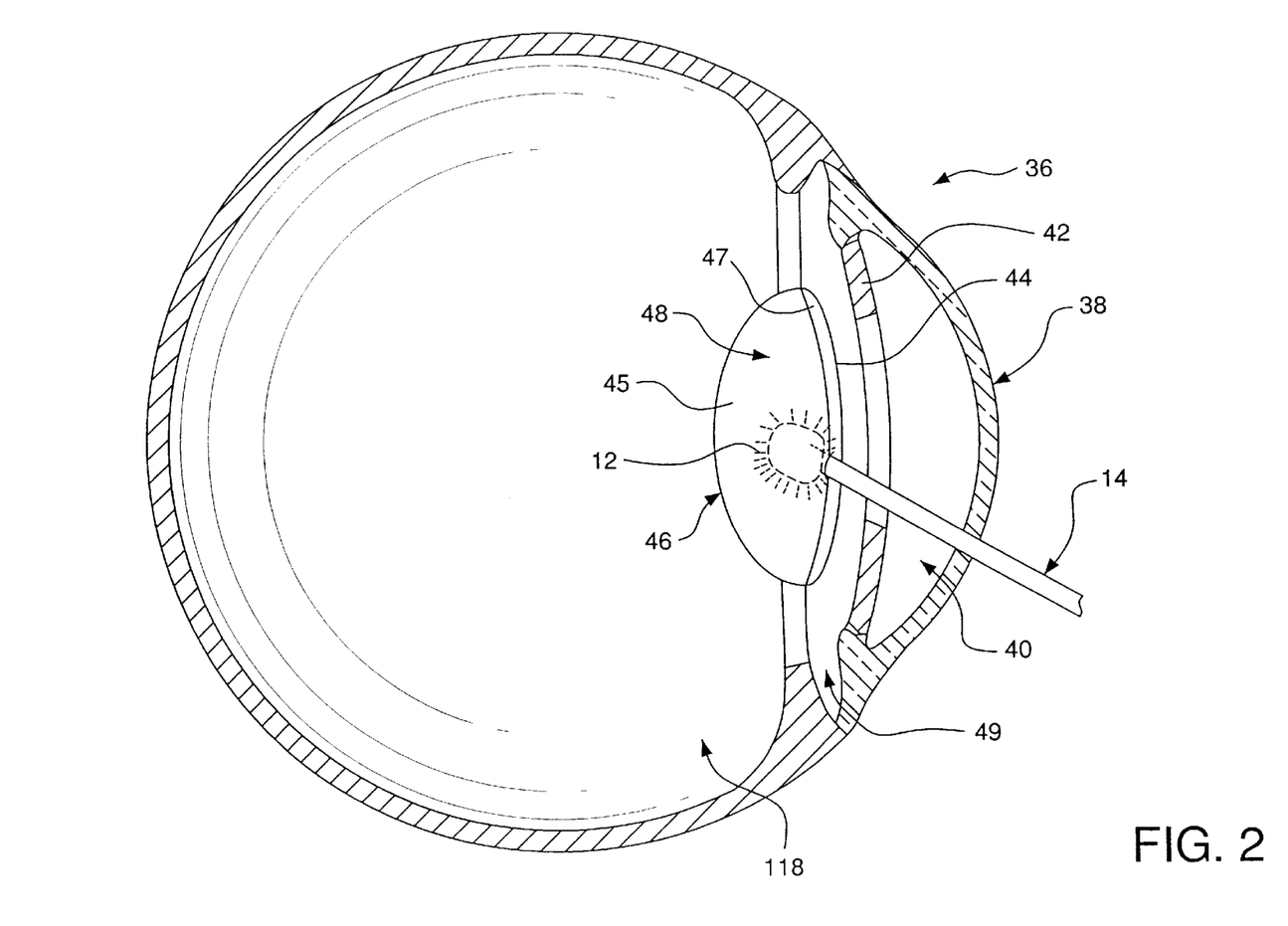
FIG. 2 is an enlarged view of a brushing device and irrigating and aspirating tubes of the system shown in FIG. 1 inserted into the lens capsule of an eye.

Referring initially to FIGS. 1 and 2, a system 10 for removing cataract has cleaning instrument such as a brush 12 coupled to one end of a tube or catheter 14 and a manifold or joint 18 coupled to the other end of tube 14. Manifold 18 has two more tubes or catheters 22 and 24 extending therefrom, with tube 22 terminating into pump 20. Pump 20 is then coupled to reservoir 26 through tube or catheter 28. Tube 24 extends from manifold 18 to safety monitor 30, which is in turn is coupled to reservoir 32 by tube or catheter 34.

Tubes 22, 24, 28 and 34 are formed from synthetic material such as silicone, plastic or any other suitable material. Tubes 22, 24, 28 and 34 can be flexible or rigid as desired and are any tube or catheter that is known to one skilled in the art.

Manifold 18 is formed from synthetic material such as silicone, plastic or any other suitable rigid material. Manifold 18 can be any manifold that is known to one skilled in the art and would allow multiple tubes to be interconnected. Additionally, manifold 18 is cable of joining two tubes 22 and 24, for example that have one passageway, to a tube that has two passageways, such as tube 14.

Pump 20 is preferably a conventional reciprocating piston pump able to create a high pressure fluid jet, but may be any suitable pump.

Monitor 30 is a conventional monitor that would measure the pressure in the tube 24 and compare this pressure with the pressure of the fluid being inserted into the eye. If these pressures were significantly different, the monitor would be capable of shutting down the pump 20 and terminating the procedure. This may be necessary if some of the dislodged cells, or any other substance, were to become caught in a tube and hinder the passage of fluid or other cells.

Reservoirs 26 and 32 are substantially similar and can be any conventional reservoir for storing fluids as is known to one skilled in the art.

Figure 7:
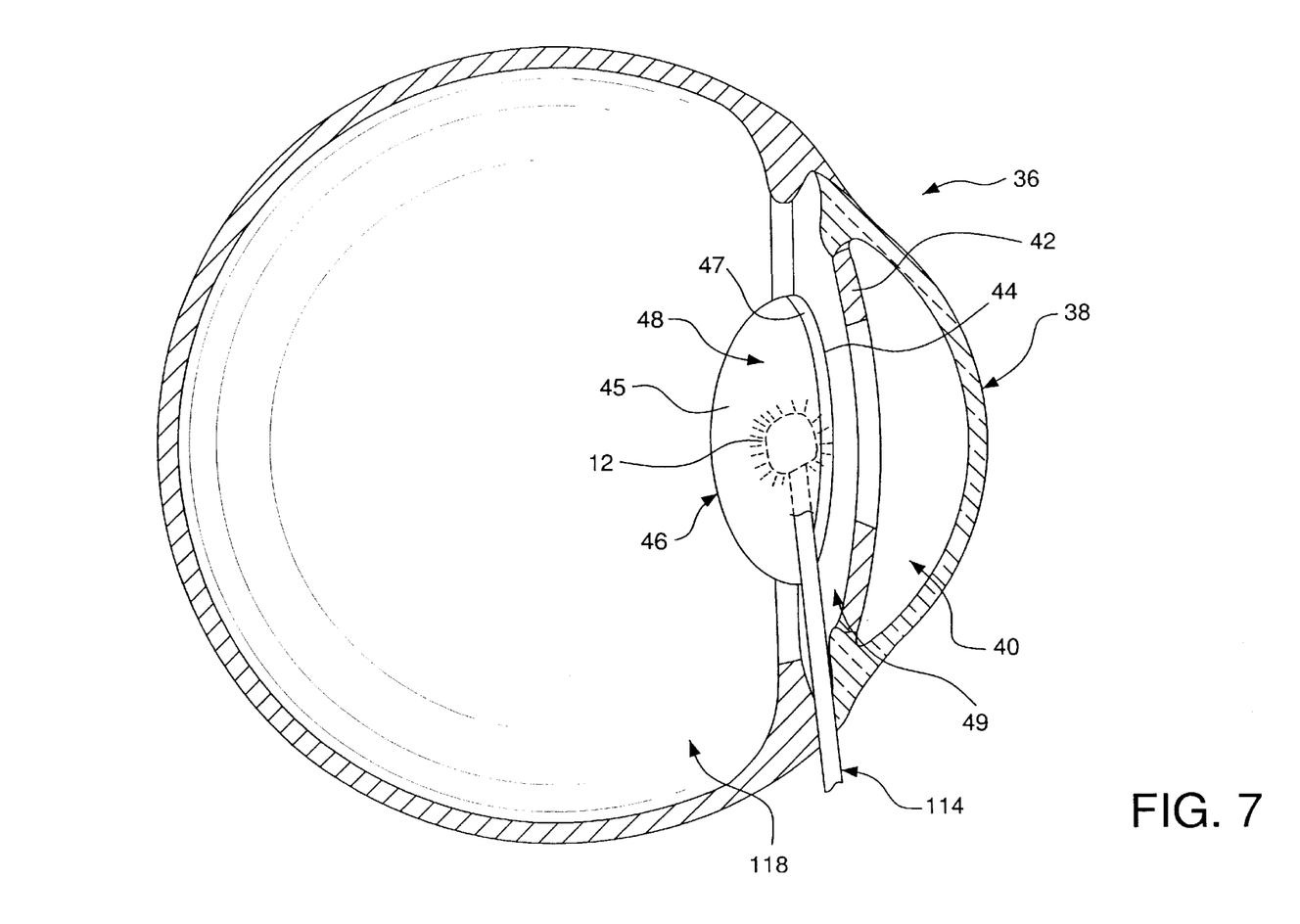
FIG. 7 is an enlarged view of the brushing device and irrigating and aspirating tubes of the system shown in FIG. 1 being inserted through a posterior chamber of the eye.

As seen specifically in FIG. 2, brush 12 can be inserted into eye 36 through cornea 38, into the anterior chamber 40, passing the iris 42 and through the surface 44 of lens 46, and thus into the lens capsule 48 where the brush 12 contacts lens fiber 45 and/or epithelial 47. Alternatively, as shown in FIG. 7 described in more detail below, the brush can be inserted into eye 36 through posterior chamber 49, behind iris 42, through the surface 44 of lens 46 and into lens capsule 48, or into the eye 36 in any other suitable manner.

Figures 3, 4:
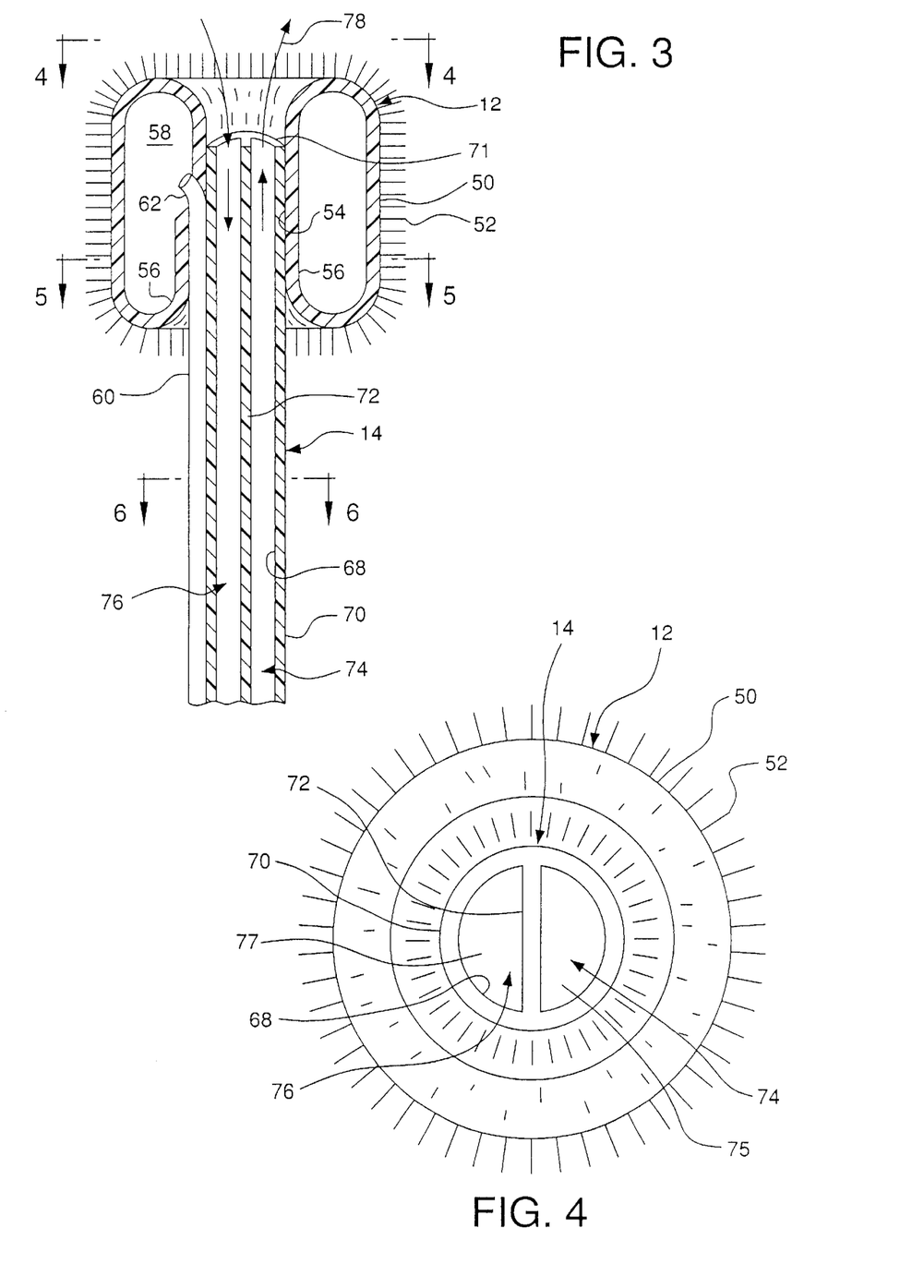
FIG. 3 is an enlarged cross-sectional side view of the brushing device and the irrigating and aspirating tubes shown in FIG. 2.
FIG. 4 is an elevational end view of the brushing device and the irrigating and aspirating tubes taken along lines 4—4 in FIG. 3.
Figure 5:
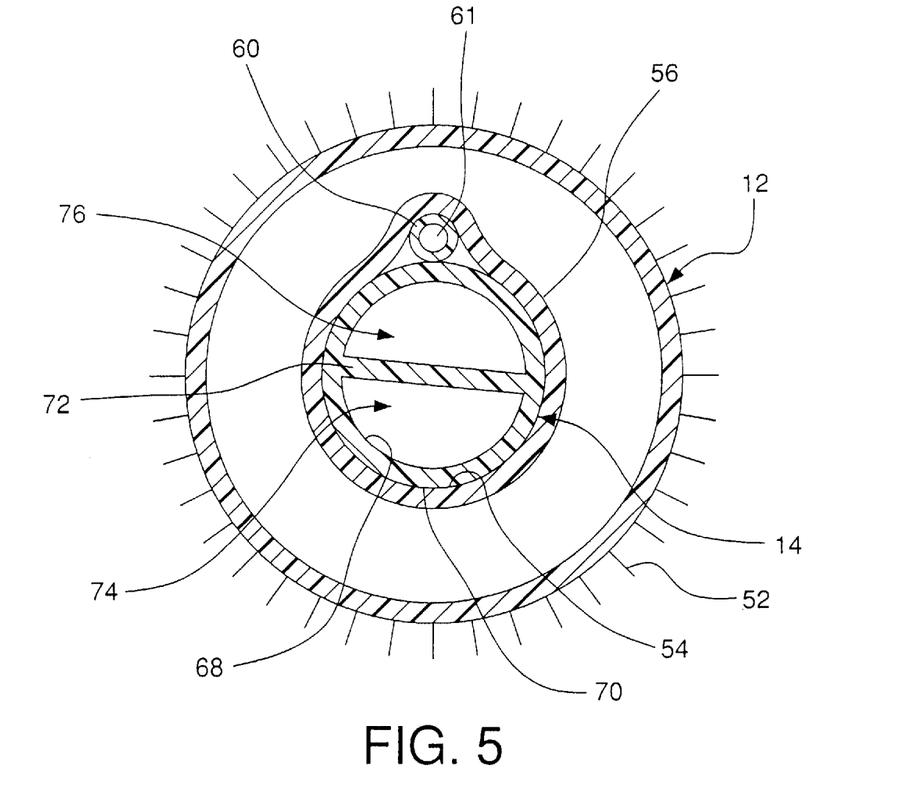
FIG. 5 is a cross-sectional view of the brushing device and the irrigating and aspirating tubes taken along lines 5—5 of FIG. 3.

Brush 12 is preferably an expandable balloon made from a synthetic material such as silicone, plastic or any other suitable expandable material, and has a fluid container allowing the balloon to be deflated and inserted through a small incision in the eye 36 and subsequently inflated with a heated fluid, such as water, saline solution or any other suitable fluid. However, brush 12 does not necessarily have to be expandable, and may be a relatively small ball at the end of tube 14, or on an outer surface of tube 14, or have any other configuration that would allow passage through a small incision in the eye 36. As seen in FIGS. 3–5, brush 12 is preferably cylindrical or substantially cylindrical having an outwardly facing exterior surface 50 with an abrasive surface or bristles 52 extending therefrom, an inwardly facing exterior facing surface 54, and an interior surface 56 defining interior chamber 58. However, brush 12 may be any suitable configuration that would enable it to couple to tube 14 and be inserted into the lens capsule of the eye 38 or any other chamber in the eye 38.

Surface 54 of brush 12 is preferably coupled to tube 14 and tube 60 by a bonding agent, such as glue or any other conventional method. However, brush 12 does not necessarily have to couple to tubes 14 or 60 in this manner, but can be coupled to one side of tube 14 and/or tube 60, or surround only a portion of tube 14. Brush 12 can also be disposed on a separate instrument attached to any suitable device that would allow the balloon to be inserted into an incision in eye 36.

Figure 6:
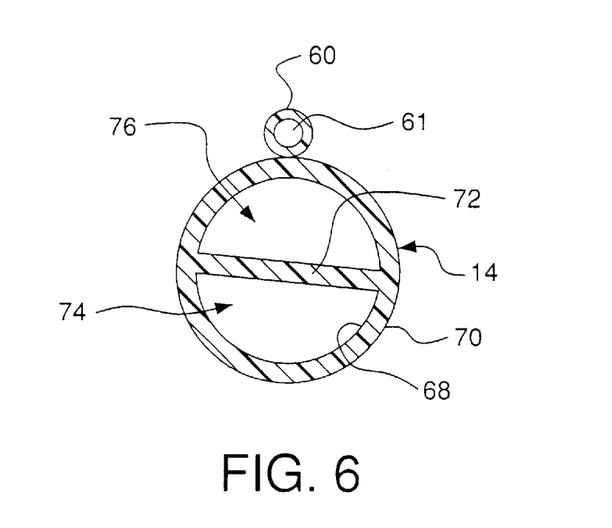
FIG. 6 is a cross-sectional view of the irrigating and aspirating tubes taken along lines 6—6 of FIG. 3.

Tube 60 extends through hole 62 in surface 56 of brush 12 and into chamber 58. Tube 60 has a through passageway 61 and is adapted to fill chamber 58 with a suitable heated fluid, such as water or saline solution. As shown in FIGS. 3, 5 and 6, tube 60 is preferably coupled and parallel to tube 14 and is formed from a synthetic material such as silicone, plastic or any other suitable material.

The heated fluid that inflates brush 12 is preferably heated to a temperature of about 5 degrees Celsius or more above the normal body temperature of 37 degrees Celsius, which causes cell death. Specifically, heating cells to a temperature of between about 42 degrees Celsius and 60 degrees Celsius, or more preferably to about 45 to 55 degrees Celsius, causes cell death. Heating cells to higher temperatures, such as about 60 degrees Celsius or higher, causes protein denaturation in the cells, which results in immediate cell death. The protein denaturation phenomenon also causes coagulation of the cells in the heated area and becomes difficult to remove, because the cells adhere tightly together.

Tube 14 may be made from a synthetic material such as silicone, plastic or any other suitable material and may have a rigid portion 64, as seen in FIGS. 1 and 2, that allows for manipulation of the brush 12, and a flexible portion 66 that allows for easier use and storage. As seen in FIGS. 3–6, tube 14 preferably has an inner surface 68, an outer surface 70, a distal end 71, and a wall 72. Wall 72 and surface 68 defining two equal or substantially equal through passageways 74 and 76. However, passageways 74 and 76 do not have to be substantially equal, and may be any size or suitable configuration that would allow a fluid to pass therethrough. Additionally, passageways 74 and 76 do not necessarily need to be disposed in the same tube, but may be two separate tubes. As shown in FIG. 3, passageway 74 is adapted to pass a fluid or liquid 78 through orifice 75 at distal end 71 and irrigate an interior chamber of the eye, while passageway 76 is adapted to allow fluid to pass through orifice 77 at distal end 71 and aspirate an interior chamber of the eye, removing any excess fluid or dislodged cells.

The fluid 78 is preferably a pressurized jet of water, saline solution or any other suitable fluid that is irrigated into the lens capsule 48 or any other area of the eye 36 using pump 20. However, the fluid 78 is not necessarily under high pressure and be under any pressure included substantially zero. Fluid 78 may be a normal balanced salt solution, a 2% alcohol solution, heated fluid of about 20 degrees Celsius to about 60 degrees Celsius (more preferably to about 40–50 degrees Celsius, even more preferably to about 42–43 degrees Celsius). Heating fluid to bout 42–42 degrees Celsius is the optimum temperature for killing the cells in the interior of the eye without causing protein denaturation in the remaining healthy cells. Additionally fluid 78 can be an enzyme, such as plasmin, tissue plasminogen activator, urokinase, and chondrotinase, or antibiotics such as, aminoglycosides and gentamycin. Fluid 78 may be one or more of these substances used independently or sequentially to damage the lens epithelium. Enzymes may be used to loosen up the lens epithelium. The alcohol solution is preferably to kill the desired epithelial cells and further loosen their attachment to the lens capsule. Heated water or saline may be used to denaturize the cell's protein and wash out the lens epithelium. While the use of aminoglycoside or gentamycin help the cells damaged membrane and promote infection prophylaxis. The use of these solutions in a sequentially removes the lens fiber and the epithelial from the lens capsule without causing protein denaturization. In addition, tubes 22, 24, 28 and 38 preferably have one passageway as it is necessary to only move fluid or liquid in one direction therethrough, but can have two passageways in a substantially similar configuration to tube 14.

Operation

Initially, a relatively small incision (approximately 2–3 mm) is preferably made through the limbus, but may be through any other portion of the cornea 38 or of the eye 36 using a lancet or any other suitable knife. The lancet or knife is preferably a separate instrument, but may be attached to the brush 12 or tube 14 or any other suitable device. Another relatively small incision of a predetermined size, similar to that above, is made in the surface of the lens capsule. As seen in FIGS. 1 and 2, the brush 12 and tubes 14 and 60 are then inserted through the incisions and the brush is inflated with an appropriate fluid. The fluid is of a temperature, described above, that heats the balloon to a desired temperature and kills the cells with which it comes into contact. Additionally, the abrasive surface or bristles 52 on the brush may be used to scrape and dislodge the lens epithelial 47 or other unwanted cells. Pump 20 is then activated, pumping water from the reservoir 26, through the manifold 18 and into passageway 74 of tube 14. The pump preferably creates pressurized jet of fluid 78, which dislodges and kills the desired cells and removes most of the lens fibers 45 and epithelium 47 in the lens capsule 48. However, the pump 20 may be used to pump the fluid 78 at any pressure, including substantially zero. As described above, the fluid may be any of the stated substances or may be a combination of the substances inserted in any desired order. Inserting a sequence of separate fluids may be accomplished by removing receptacle 26 replacing it with another containing a desired substance, or alternatively, there may be multiple reservoirs in parallel that can be activated manually, depending on which fluid is to be infused into the eye 36.

The relatively small incision in the lens capsule 48 preferably results in a semi-closed system in which the dislodged cells and the irrigated fluid are contained and removed through the aspirating passageway 76 of tube 14. However, it is not necessary for the system 10 to operate in a semi-closed system (particularly if the irrigated fluid is not pressurized). The suction needed for this passageway 76 is automatically caused by the pressure differential due to the increased pressure in the lens capsule 48 and the pressure in the passageway 76. The fluid passes through monitor 30 and into the reservoir 32.

The brush 12 and tubes 14 may then be removed and the lens capsule 48 filled with a transparent biocompatable elastic substance or a portion of the lens capsule 48 can be removed for implantation of a standard intraocular lens, in the remaining capsular portion. For a further description of intraocular lenses see U.S. Pat. Nos. 4,581,031 and 4,666,446, both to Koziol et al., the entire contents of which are herein incorporated by reference.

Figure 8:
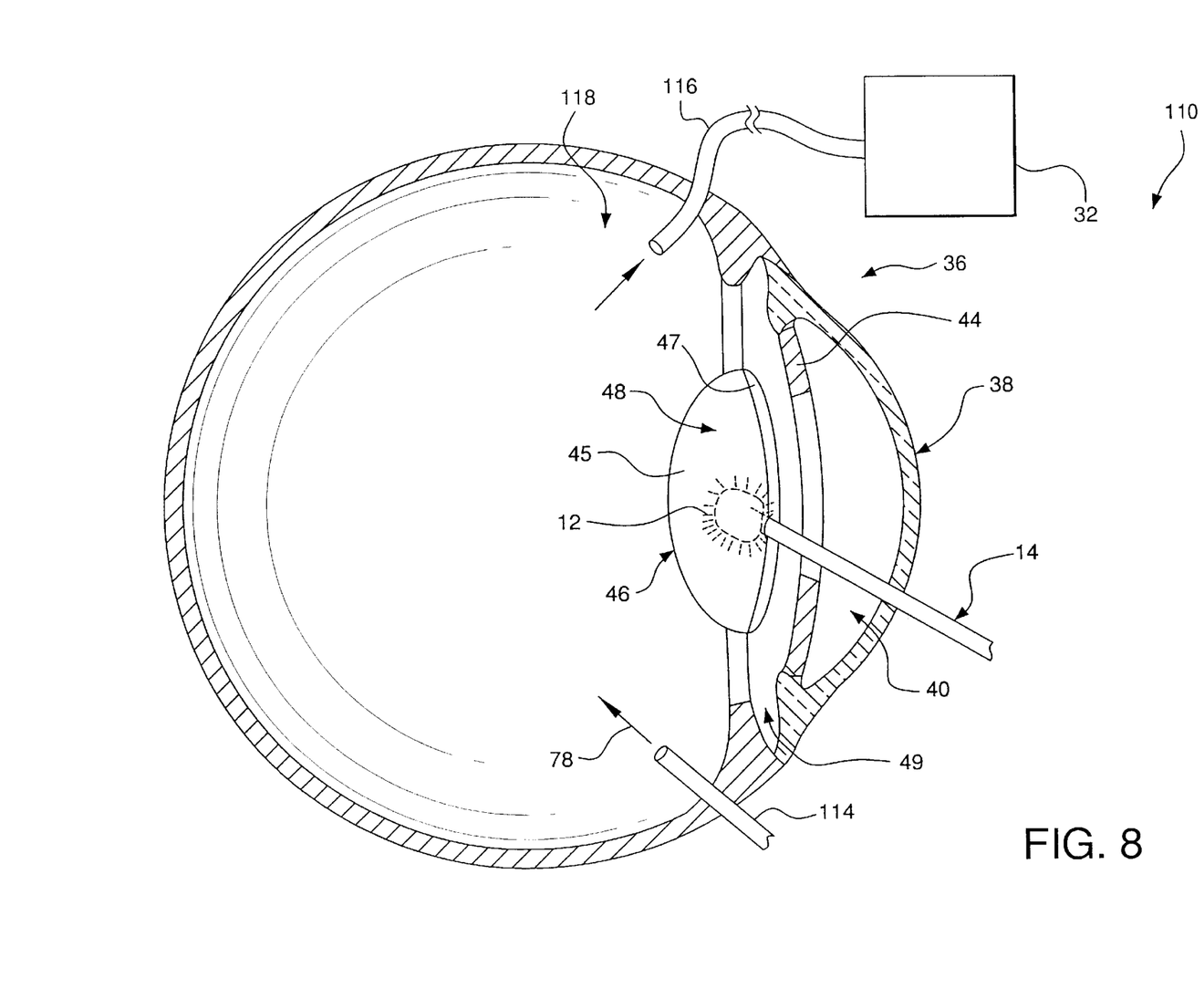
FIG. 8 is an enlarged view of the brushing device and irrigating and aspirating tubes of the system for removing cells as shown in FIG. 7 with additional aspirating and irrigating tubes being inserted into the posterior chamber of the eye.

Embodiment of FIG. 8

A system 110 according to another embodiment of the present invention will now be described. As seen in FIG. 8, system 110 has tubes 114 and 116. Tube 114 is an irrigation tube that is formed from material and produces a water jet that is substantially similar to the passageway 74 described above, the description of passageway 74 of tube 14 and fluid 78 is applicable to tube 114. Tube 116 is substantially similar to and formed from similar material as aspirating passageway 76 described above, the description of passageway 76 of tube 14 and fluid 78 is applicable to tube 116. System 110 can be used in conjunction with a system similar to system 10 described above, or it may be used alone. Operation of system 10 is similar to 110 and the description of system 10 is applicable to system 110.

In system 110, it would be necessary to cut and dislodge vitreous cells using a cutting mechanism, such as a knife or other device, as is known to one of ordinary skill in the art. Once the cells have been dislodged, system 110 could then be inserted into a chamber in the eye. As seen in FIG. 8, system 110 injects fluid 78 into the vitreous 118 on an eye 36 irrigating cells therein. These dislodged cells and the fluid injected into the eye are then aspirated using tube 116, in a substantially similar manner as described above for aspirating passageway 76.

Additionally, system 110 or system 10 described above can have a fiber optic cable (not shown) attached to tube 114 or tube 116 to illuminate the area in which the sells are to be removed. The fiber optic cable does not necessarily have to be coupled to a tube, and may be a separate instrument. System 110 may also have a guide wire (not shown) to add rigidity and control to system 110.

Embodiment of FIGS. 9–16

Figure 9:
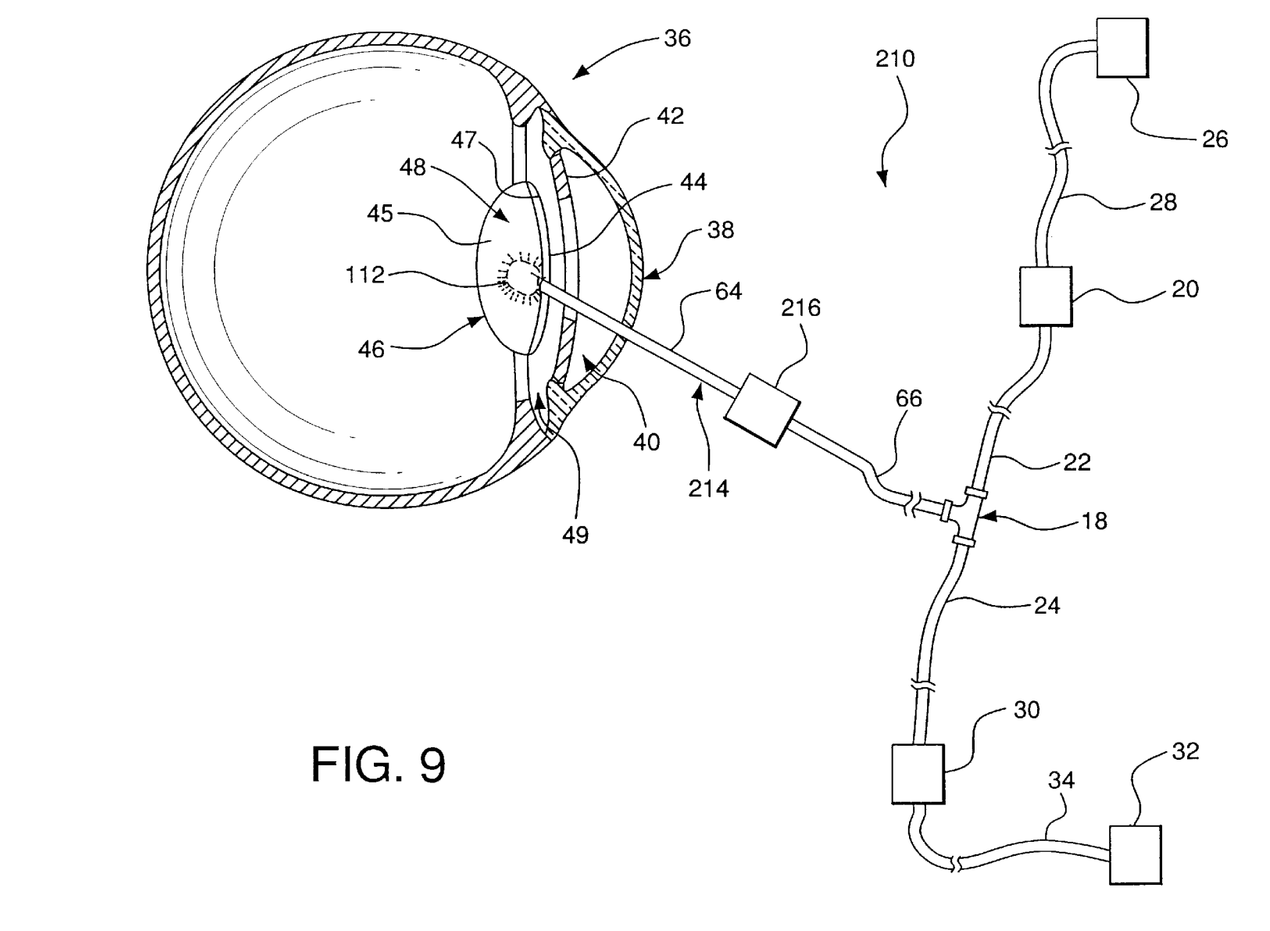
FIG. 9 illustrates a system for removing cells according to another embodiment of the present invention, which is being inserted into the lens capsule of an eye.

A further embodiment of the present invention will now be described. As seen in FIGS. 9–13, system 210 has a brush 212 and a tubes 214 and 260 substantially similar to brush 12, tube 14, and tube 60, respectively, and any description of brush 12 and tubes 14 and 60 above applies to brush 212 and tubes 214 and 260. Additionally, brush 212 is disposed in a system substantially similar to system 10 and the description of system 10 applies to system 210. However, as seen in FIG. 9, this embodiment employs a motor 216 as described in more detail below.

Figures 10, 11:
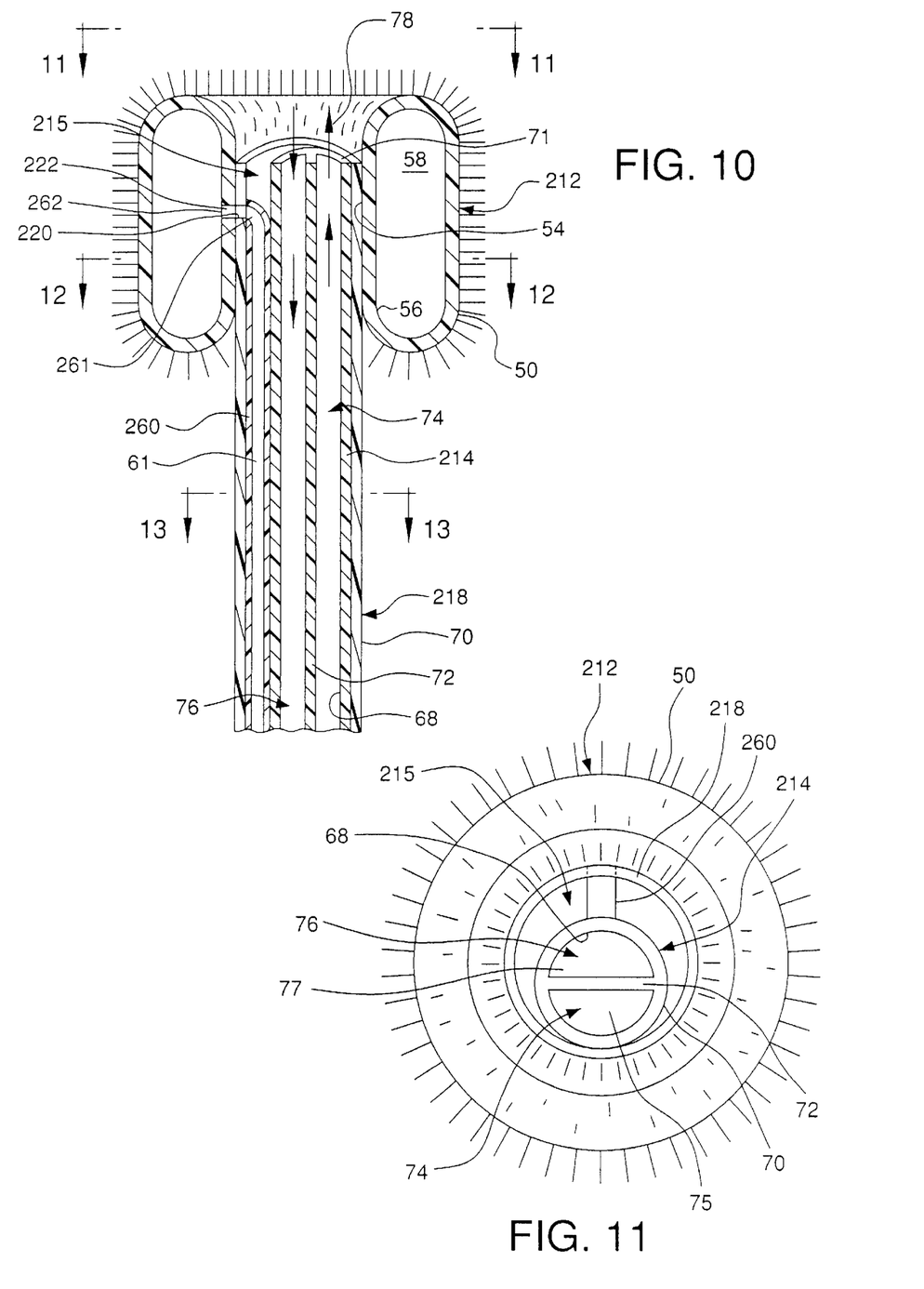
FIG. 10 is an enlarged cross-sectional side view of the brushing device and the irrigating and aspirating tubes of the system shown in FIG. 9, in which the brush moves relative to the irrigating and aspirating tubes.
FIG. 11 is an end elevational view of the brushing device and irrigating and aspirating tubes taken along lines 11—11 of FIG. 10.
Figure 12:
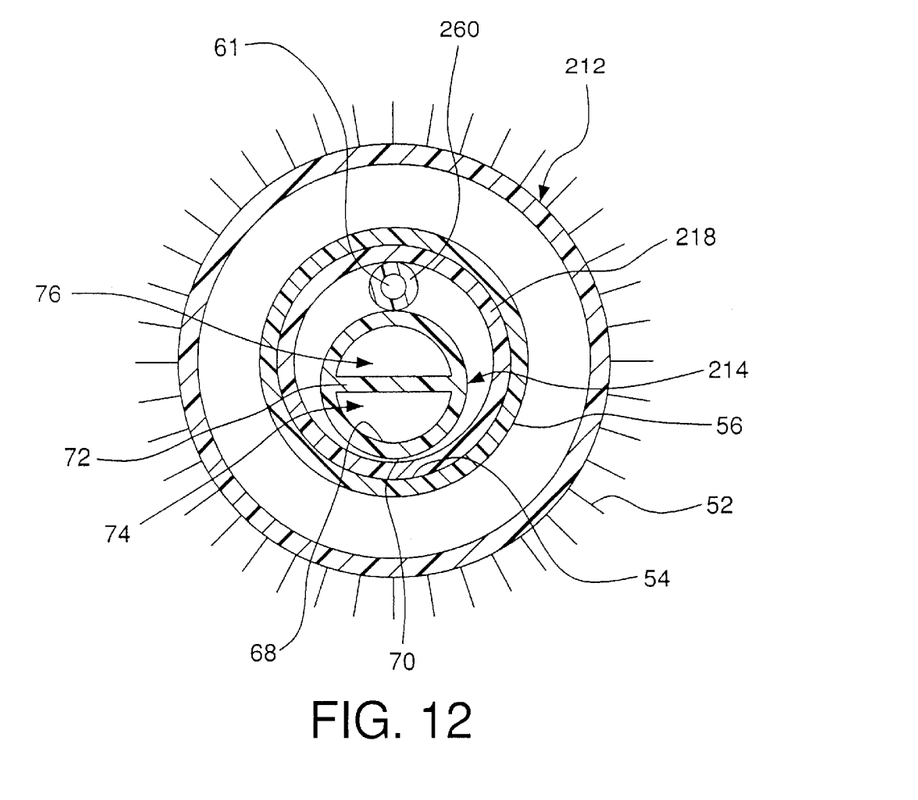
FIG. 12 is a cross-sectional view of the brushing device and irrigating and aspirating tubes taken along lines 12—12 of FIG. 10.
Figure 13:
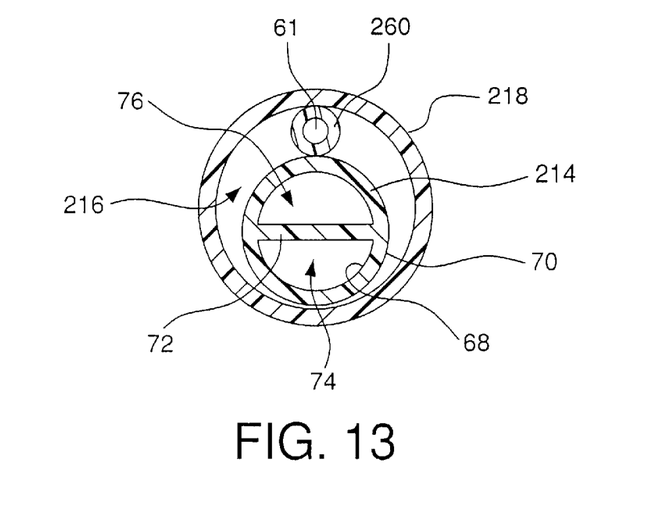
FIG. 13 is a cross-sectional view of the irrigating and aspirating tubes taken along lines 13—13 of FIG. 10.

As seen in FIGS. 10–12, tubes 214 and 260 are disposed in a cavity or chamber 215 of outer tube 218. Brush 212 is coupled to tube 218 in the same manner as brush 12 is coupled to tube 14 described above. Tube 218 is made from a synthetic material such as silicone, plastic or any other suitable material and has a hole 220 that along with hole 262 of brush 212 defines through passageway 222. Open end 261 of tube 260 is adapted to align with through passageway 222 and allows a heated fluid such as water to inflate brush 212. The heated fluid used to inflate brush 212 is substantially similar to the heated fluid to inflate brush 12 and the description thereof is applicable to this embodiment.

Figure 14:
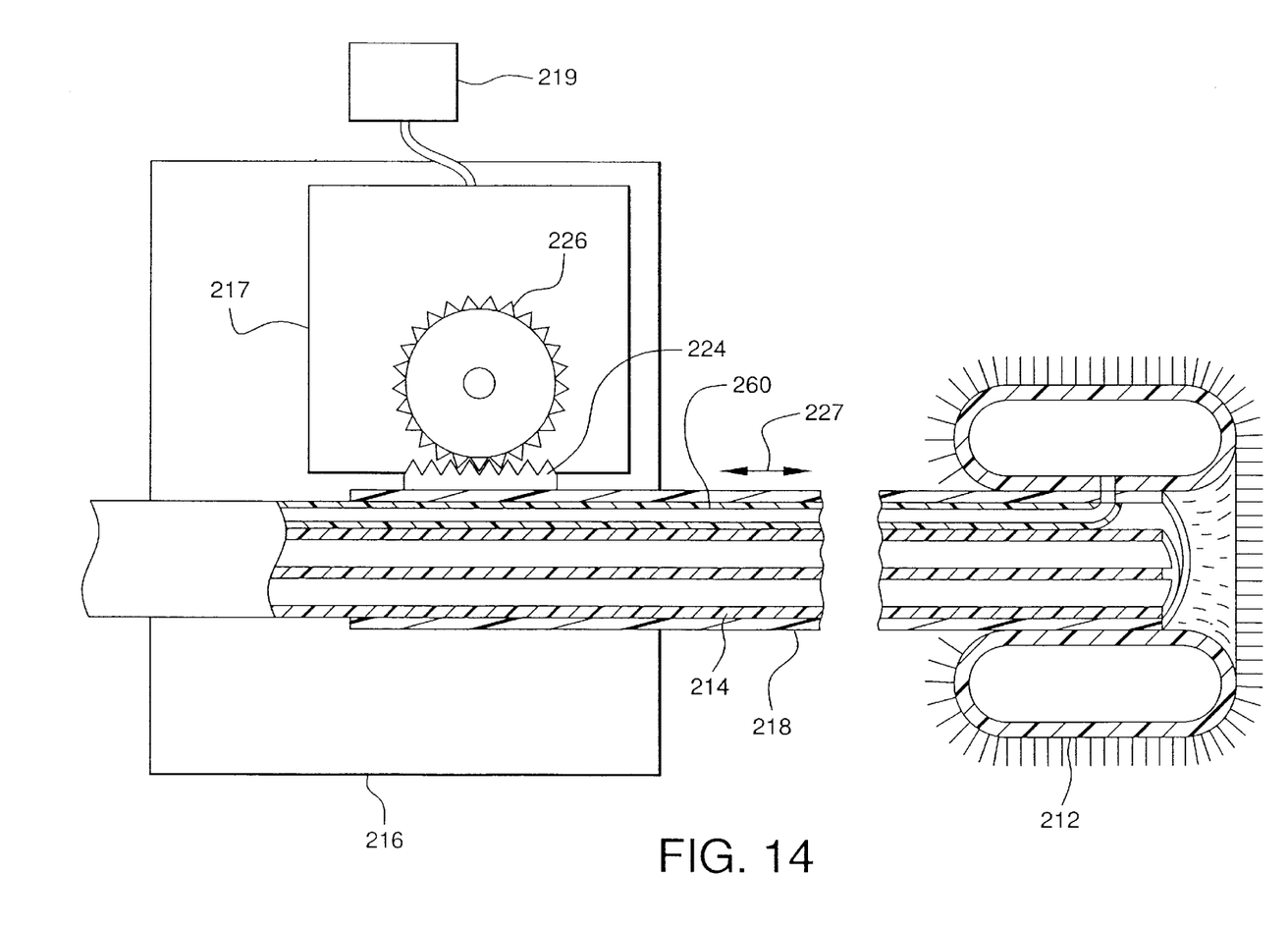
FIG. 14 is a cross-sectional side view of the system shown in FIG. 9, modified such that the brushing device oscillates relative to the aspirating and irrigating tubes.

As seen in FIG. 14, outer tube 218 has a series of teeth 224 coupled to the exterior surface. These teeth engage a gear 226 coupled to electric motor 217, the combination adapted to reciprocate tube 218 and brush 212 connected thereto in the directions of arrows 227. Electric motor 217 may be adapted to oscillate brush 212 at frequencies ranging from about one cycle per second up to several thousand cycles per minute. This motion or movement allows the brush to move back and forth with respect to tube 212 and the remainder of the system, and assist in dislodging lens fiber 45 and epithelial cells 47 from the lens capsule 48.

As seen in FIG. 14, electric motor 217 is electrically coupled to a controller 219 that controls the frequency of the oscillations of brush 212 and can turn the electric motor 217 on and off.

Figure 15:
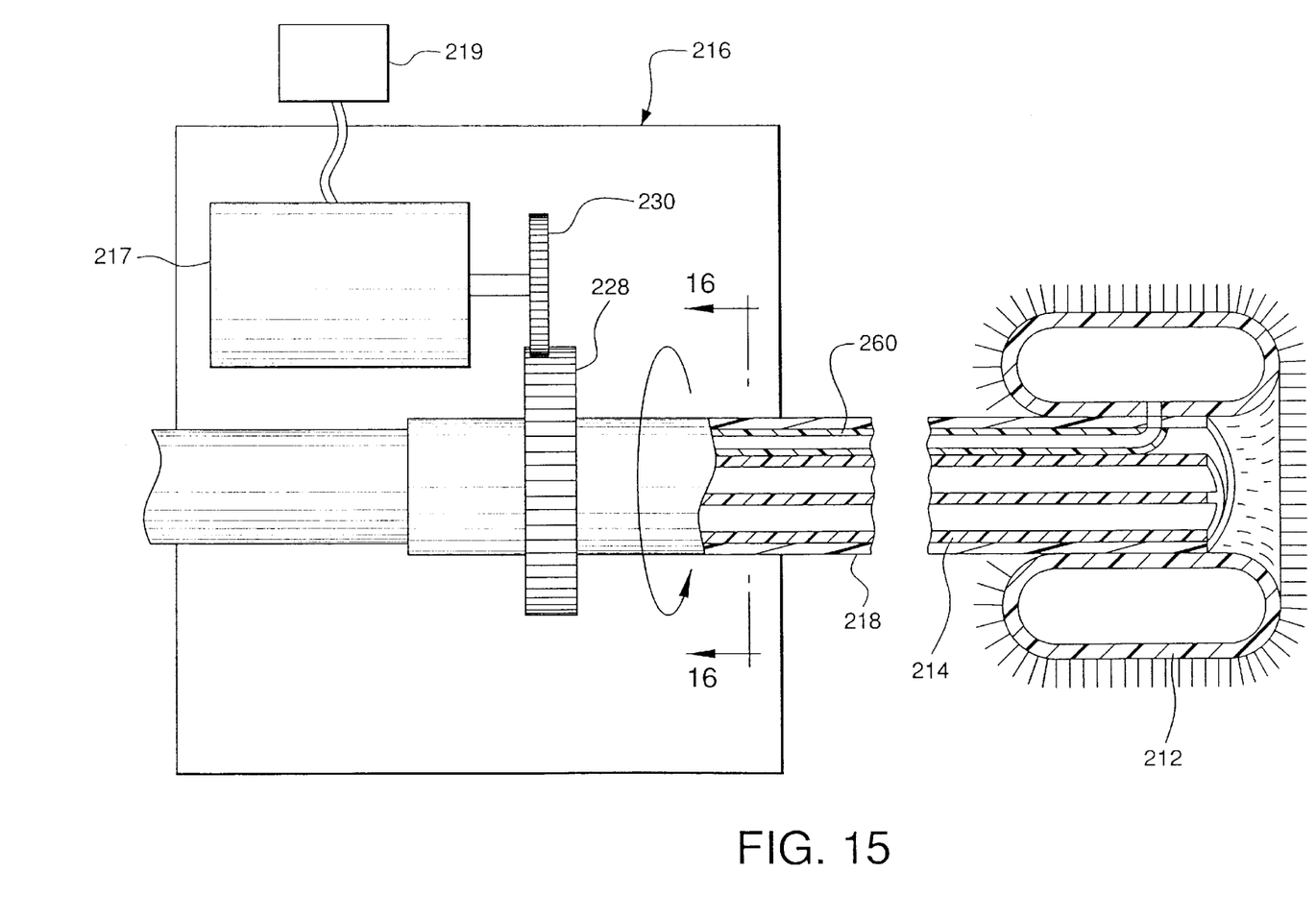
FIG. 15 is a cross-sectional side view of the system of FIG. 9, modified such that the brushing device rotates relative to the aspirating and irrigating tubes.
Figure 16:
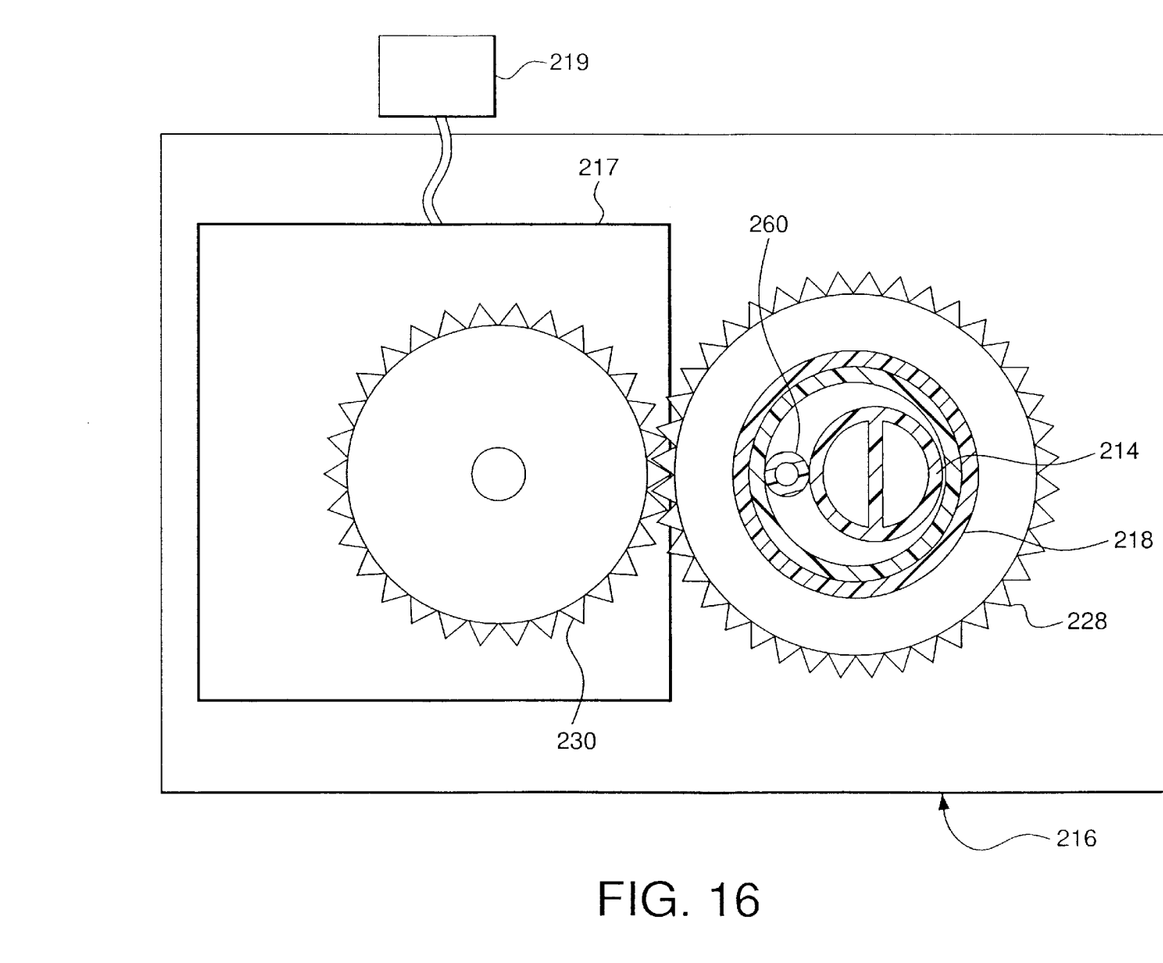
FIG. 16 is a cross-sectional view of the system of FIG. 14 taken along lines 16—16.

As seen in FIGS. 15 and 16, a gear 228 is coupled to and surrounds tube 218 and engages gear 230 that is connected to electric motor 217. This combination allows tube 218 and the brush 212 coupled thereto to rotate with respect to tubes 214 and 260 and the remainder of the system and assist in dislodging lens fiber 45 and epithelial cells 47 from the lens capsule 48. Electric motor 217 may be adapted to rotate brush 212 at a rate ranging from about one rotation per second up to several thousand rotations per minute.

As seen in FIGS. 15 and 16, electric motor 217 is electrically coupled to a controller 219 that controls the rate of the rotation of brush 212 and can turn the electric motor 217 on and off.

These two examples of motion of the tube 218 and the brush 212 with respect to the tube 214 are examples only and do not limit the brush and tube from other movement or combinations of movement, such as a gear configuration that would allow the brush to simultaneously or sequentially rotate and/or oscillate.

Embodiment of FIGS. 17–20

A further embodiment of the present invention will now be described. As seen in FIGS. 17–20, system 310 has a brush 312 and tubes 314 and 360. Brush 312 and tube 360 are substantially similar to brush 12 and tube 60, respectively, and any description of brush 12 and tube 60 above applies to brush 312 and tubes 314 and 360. Additionally, brush 312 is disposed in a system substantially similar to system 10 and may be disposed in a system substantially similar to system 210 and the descriptions of systems 10 and 210 apply to system 310.

Tube 314 may be made from a synthetic material such as silicone, plastic or any other suitable material. Tube 314 preferably has an inner surface 368, an outer surface 370, a closed distal end 371, a wall 372, and preferably two apertures 380 and 382 extending from outer surface 370 to inner surface 368. Wall 372 and surface 368 define two equal or substantially equal through passageways 374 and 376. However, passageways 374 and 376 do not have to be substantially equal, and may be any size or suitable configuration that would allow a fluid to pass therethrough. Additionally, passageways 374 and 376 do not necessarily need to be disposed in one tube and may be individual tubes either separated or coupled together. Aperture 380 extends through outer surface 370 and into passageway 374 and preferably, aperture 382 extends through the outer surface 370 and into passageway 376. However, it is not necessary to have aperture 382, as described below. Apertures 380 and 382 may be any size or configuration that would allow fluid 378 and cells within the eye 36 to pass therethrough. Apertures 380 and 382 may also be placed anywhere along the length or periphery of tube 314 or there may be multiple apertures extending through surface 370 and into each passageway 374 and 376, as deemed necessary. Wall 372 extends substantially the entire length of tube 314, however it does not extend to and abut end 371. Wall 372 terminates a predetermined distance from end 372 leaving a passage 375 between passageways 376 and 374, allowing fluid and lens cells or any other cells to pass from passageway 374 to passageway 376.

Figures 17, 18:
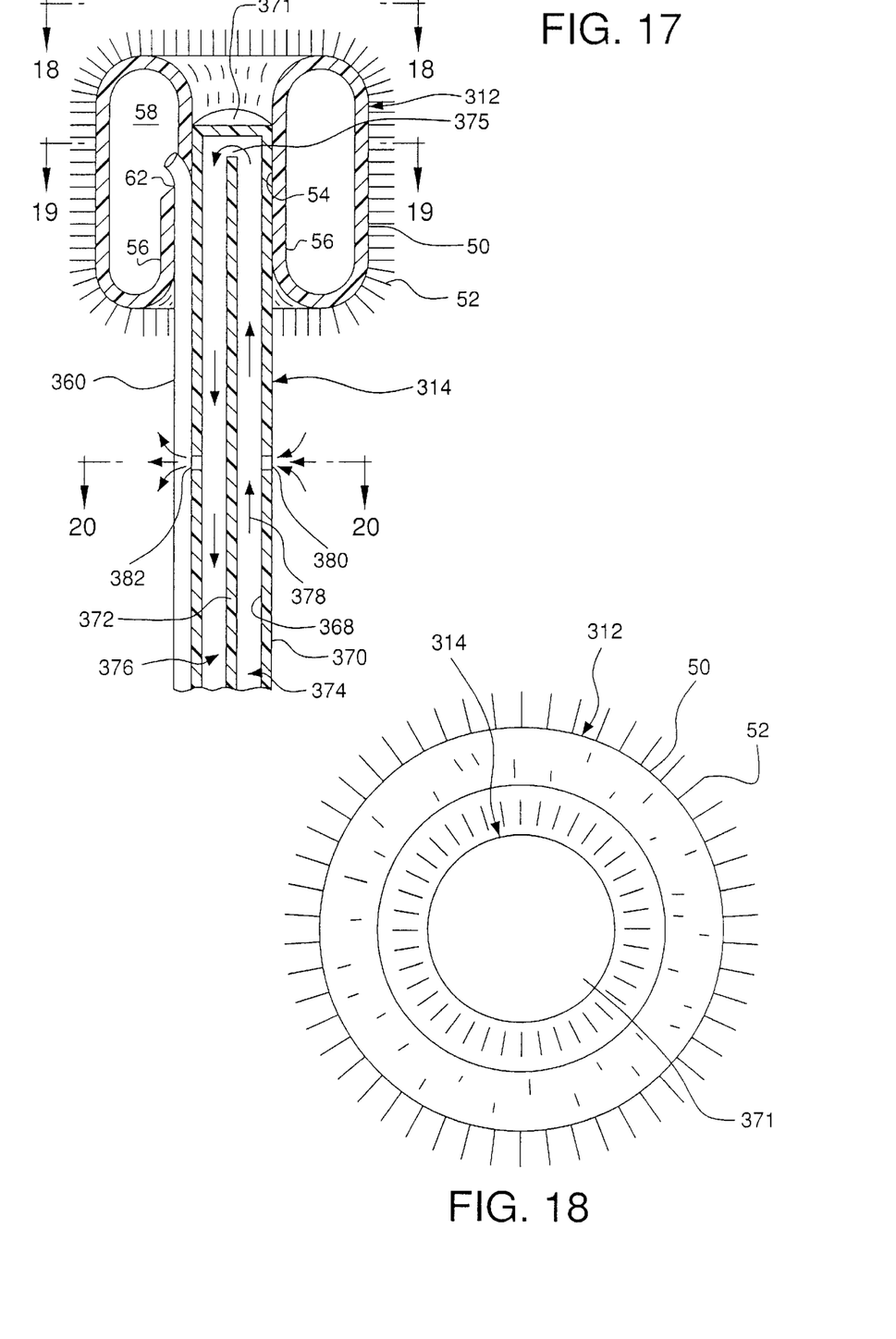
FIG. 17 is a cross-sectional side view of a brushing device and the high pressure fluid system according to another embodiment of the present invention.
FIG. 18 is an elevational end view of the brushing device and the high pressure and return tubes taken along lines 18—18 in FIG. 17.
Figure 19:
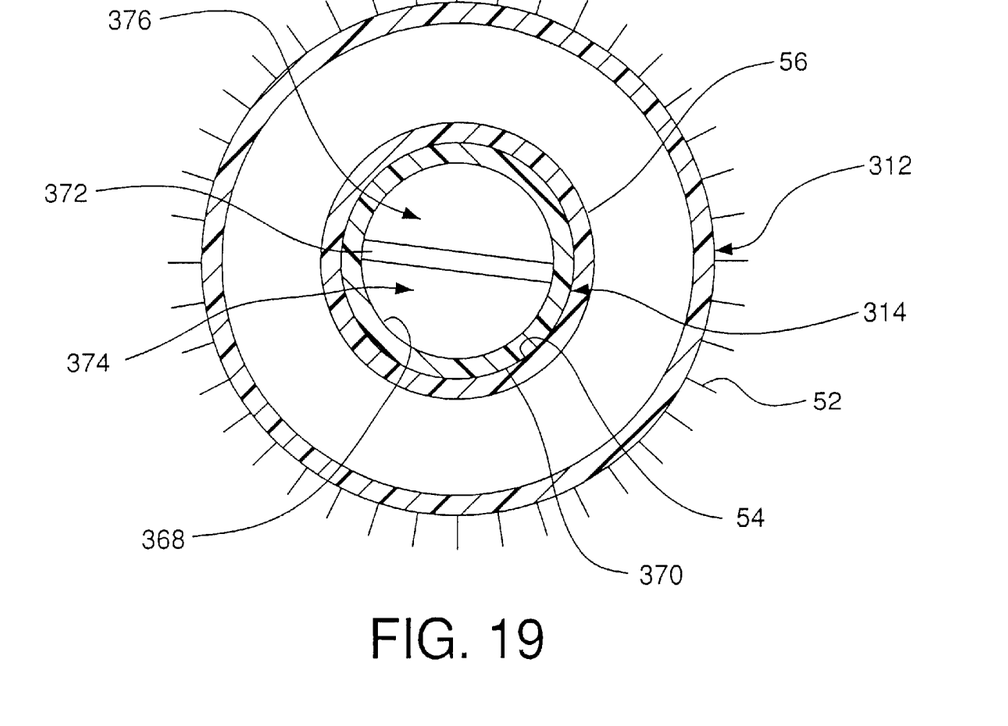
FIG. 19 is a cross-sectional view of the brushing device and the high pressure and return tubes taken along lines 19—19 of FIG. 17.
Figure 20:
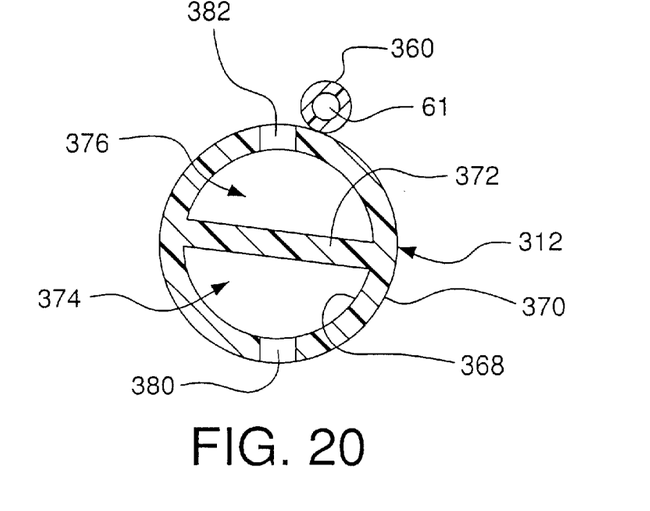
FIG. 20 is a cross-sectional view of the high pressure and return tubes taken along lines 20—20 of FIG. 17.

Similar to system 10 above, brush 312 and tube 314 are inserted into a semi-closed lens capsule 48 and brush 312 is inflated and used to dislodge cells, such as lens epithelial 47 or lens fiber 45 or any other desired cells. Using a high pressure pump substantially similar to pump 20, described above for system 10, a fluid 378 is pumped into tube 314, or more specifically passageway 374, under high pressure. Fluid 378 is substantially similar to fluid 78 and the description thereof applies to fluid 378. As fluid 378 flows through passageway 374 it passes aperture 380 creating suction at aperture 380, while allowing no or minimal fluid to pass through the aperture 380. The suction at aperture 380 draws fluid (i.e. the minimal fluid that passes through aperture 380 or fluid that passes through aperture 382, described in more detail below) and cells into passageway 374. The cells that are drawn in may be any cells dislodged or cellularly attached in the eye. The cells may be epithelial cells, cell fiber, or any other cells to be removed from the interior of the eye. Once the cells are drawn into passageway 374 they are cut or dislodged from the lens capsule 48 or any other portion of the eye by the high pressure fluid flow and similarly swept away. The flow contacts the closed end 371 and passes through passageway 375 and into passageway 374, where it returns to reservoir 32, if there is no aperture 382. Preferably, however, there is another aperture 382 in passageway 376. In which case, since the fluid in passageway 376 will not be under high pressure, some of the fluid and/or cells may escape through aperture 382, most of the fluid and cells return to reservoir 32, similar to the systems 10 and 210 described above. However, the material and fluid that escapes through aperture 382 is released into the semi-closed lens capsule system and returns into the suction aperture 380. As this process repeats itself, a decreasing number of the cells from the eye escape back into the lens capsule until virtually no cells escape from the aperture 382.

The use of the high pressure system to cut and cycle the fluid 378 may be used before, after or during the use of brush 312. It is not necessary for the use of the tube to follow the use of the brush and they may be alternately used in any order, any number of times.

Additionally, it is possible to use tube 314 without brush 312, in the lens capsule 48, as described above, or to remove vitreous in the eye as described in the embodiment of FIG. 8. If tube 314 were used to remove vitreous, it would not be necessary to cut or dislodge the vitreous prior to insertion of tube 314 into the eye, as described above. The high pressure water system would cut and dislodge the vitreous and remove the cells therefrom.

The features of systems 110, 210, and 310, which are similar to system 10 are identified with like reference numbers. The same description of those similar features is applicable.

While a few specific embodiments have been chosen to illustrate the invention, it will be understood by those skilled in the art that various changes and modifications can be made therein without departing from the scope of the invention as defined in the appended claims.

What is claimed is:

1. A high pressure system adapted for insertion into an eye for removing cells from an interior of the eye, comprising:
   a first passageway having a first aperture, said passageway being adapted to pass a high pressure fluid therethrough, said high pressure fluid flowing adjacent said first aperture and causing a suctioning force therethrough, said first aperture adapted to allow cells to pass therethrough and into said first passageway, and said suctioning force being adapted to dislodge cells from the eye; and
   a second passageway for removing said fluid and dislodged cells out of the eye.

2. A high pressure system according to claim 1, wherein:
   said first and second passageways are coupled together.

3. A high pressure system according to claim 1, wherein:
   said first and second passageways are disposed within a first tube system.

4. A high pressure system according to claim 3, wherein:
   said second passageway has a second aperture therethrough, said second aperture adapted to allow fluid and cells to pass therethrough.

5. A high pressure system according to claim 1, further comprising:
   an instrument adapted to pass through an incision in said eye and having a surface adapted to contact and dislodge cells from said interior of said eye.

6. A high pressure system according to claim 5 wherein:
   said instrument includes a fluid container, adapted to receive and contain a heated fluid therein.

7. A high pressure system according to claim 6, further comprising:
   a second tube system coupled to said instrument, and having a third passageway for inserting said heated fluid into said fluid container.

8. A high pressure system according to claim 5, wherein:
   said instrument is adapted to oscillate relative to said first tube.

9. A high pressure system according to claim 5, wherein:
   said instrument is adapted to rotate relative to said first tube.

* * * * *